United States Patent
Tanaami

(10) Patent No.: US 6,955,881 B2
(45) Date of Patent: Oct. 18, 2005

(54) METHOD AND APPARATUS FOR PRODUCING BIOCHIPS

(75) Inventor: Takeo Tanaami, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 434 days.

(21) Appl. No.: 10/251,388

(22) Filed: Sep. 20, 2002

(65) Prior Publication Data
US 2003/0017496 A1 Jan. 23, 2003

Related U.S. Application Data

(62) Division of application No. 09/631,609, filed on Aug. 4, 2000, now abandoned.

(30) Foreign Application Priority Data

Sep. 3, 1999 (JP) .................................. 11-250213
May 26, 2000 (JP) ............................. 2000-156231

(51) Int. Cl.⁷ ........................... C12Q 1/68; C12M 1/36; G01N 15/06; B01L 3/02
(52) U.S. Cl. ........................ 435/6; 435/174; 435/283.1; 435/287.2; 422/68.1; 422/82.01; 422/100
(58) Field of Search ............................ 435/6, 7.1, 174, 435/283.1, 287.2; 422/68.1, 100, 82.01

(56) References Cited

U.S. PATENT DOCUMENTS

| | | | |
|---|---|---|---|
| 5,486,337 A * | 1/1996 | Ohkawa ...................... | 422/100 |
| 5,981,733 A * | 11/1999 | Gamble et al. ............. | 536/25.3 |
| 6,284,113 B1 * | 9/2001 | Bjornson et al. ........... | 204/453 |
| 6,594,432 B2 * | 7/2003 | Chen et al. .................. | 385/133 |

* cited by examiner

Primary Examiner—BJ Forman
(74) Attorney, Agent, or Firm—Moonray Kojima

(57) ABSTRACT

A method and apparatus for mass producing biochips quickly and easily, wherein a plurality of DNA molecules are amplified using a PCR (polymerase chain reaction) method and transcribing the amplified DNA molecule to other substrates by contact.

4 Claims, 6 Drawing Sheets

FIG. 1
PRIOR ART
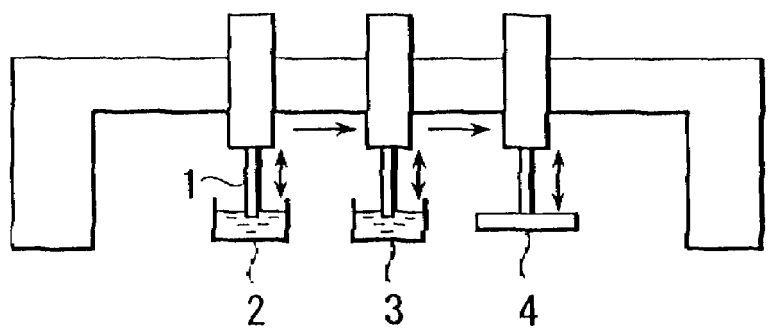
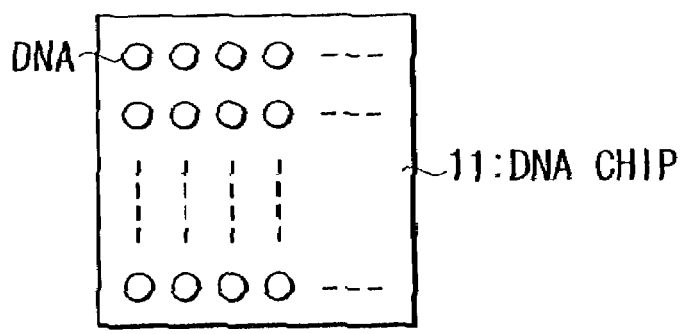
FIG. 2A
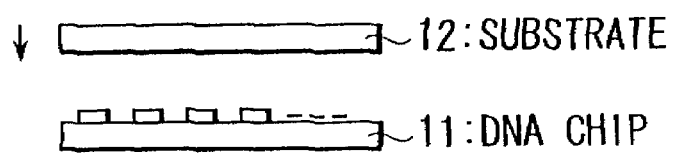
FIG. 2B
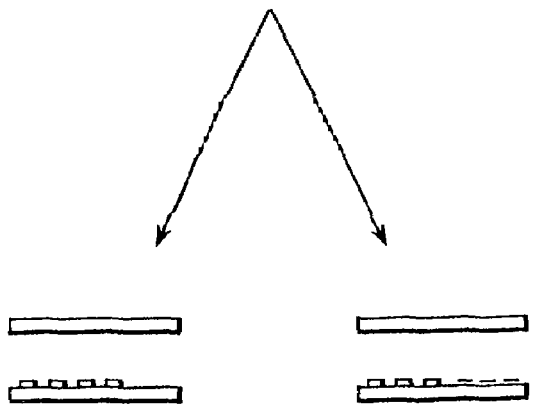
FIG. 2C

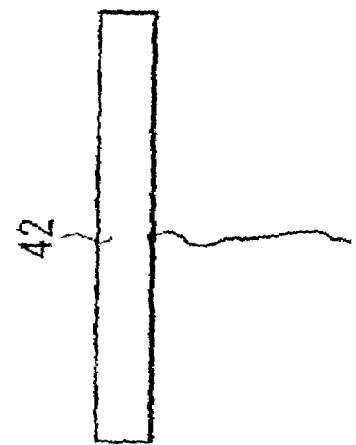
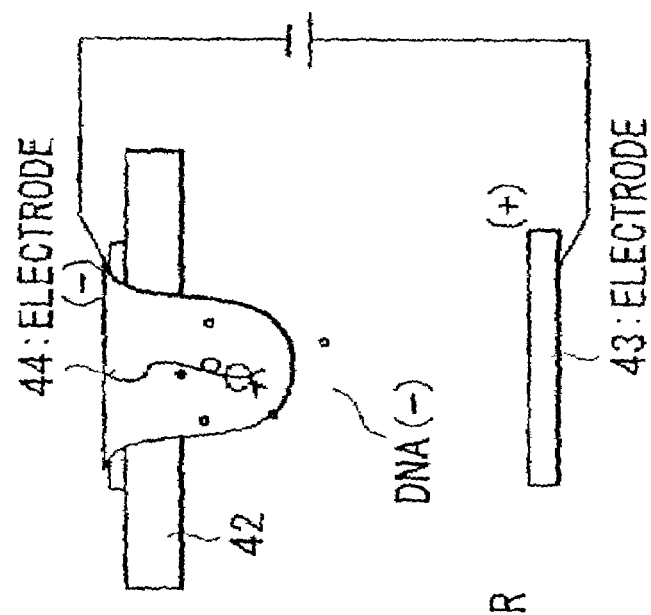
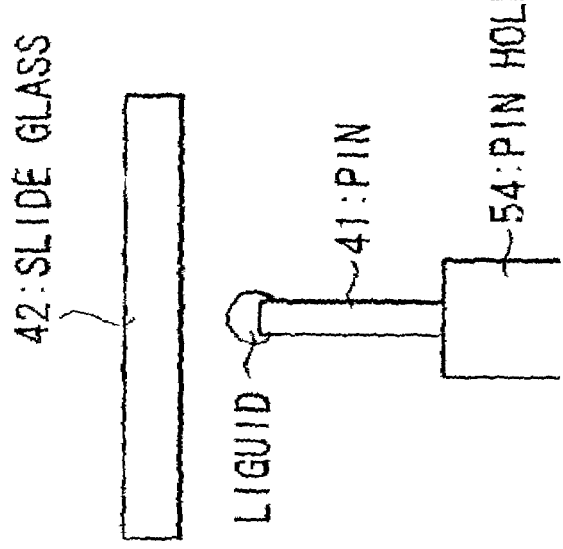

METHOD AND APPARATUS FOR PRODUCING BIOCHIPS

RELATED APPLICATIONS

This application is a Divisional Application of Ser. No. 09/631,609 filed Aug. 4, 2000, now abandoned.

BACKGROUND OF THE INVENTION

1. Field of Invention

This invention relates to improvements in methods and apparatus for producing biochips, such as biomolecules, such as DNA, RNA, protein and sugar chain molecules, which are arranged in arrays on a substrate.

2. Description of the Prior Art

The prior art can be understood by taking DNA chips as an example. Generally, DNA chips are 1 to 10 $cm^2$ in size and several thousand to several hundred thousand types of DNA segments are arranged within the area of such chips. One conventional method of producing the biochips comprises the steps of stamping and depositing a solution of DNA segments prepared by a polymerase chain reaction (henceforth referred herein as "PCR") onto a slide glass or silicon substrate using pins on an arrayer, or by synthesizing a large quantity of DNA segments at one time on a glass substrate using semiconductor techniques.

FIG. 1 shows conventional method, wherein the tip of pin 1 is first dipped in a washing fluid contained in chamber 2, for cleaning the pin tip. Next, pin 1 is moved to a solution chamber 3 and dipped thereinto so that DNA segments are caused to adhere to the tip of pin 1. Finally, pin 1 is moved and pressed on a slide glass 4 to produce a DNA chip.

The prior art methods are plagued with problems, such as, for example:

(1) The process of deposition of the DNA segments using a pin consumes a long length of time, and the quality of a stamped site (referred to hereinafter as "cell" or "spot" or "site") is not uniform. Moreover, it is difficult to deposit only a small amount of DNA solution. Thus, waste becomes a factor.

(2) The method of synthesizing a large quantity of DNA segments at one time on a glass substrate by using semiconductor techniques requires large scale factory equipment. Thus, cost becomes a large factor.

SUMMARY OF THE INVENTION

Accordingly, an object of the invention is to overcome the aforementioned and other deficiencies and disadvantages of the prior art.

Another object is to provide a method and apparatus for rapidly and easily mass produce biomolecular chips with uniform quality.

BRIEF DESCRIPTION OF THE DRAWINGS

FIG. 1 is a diagram depicting a prior art method of producing biochips.

FIGS. 2(A)–2(C) are views depicting a first illustrative embodiment of the method of the invention.

FIGS. 10(A)–10(C) are views depicting a seventh illustrative embodiment of the method of the invention.

DETAILED DESCRIPTION OF THE PREFERRED EMBODIMENTS

In FIG. 2(A), the DNA is amplified by a PCR method on a DNA chip 11 serving as a mother substrate. Then, the DNA chip 11 is brought into direct contact with a copy substrate 12 and copied, as shown in FIG. 2(B), while concurrently maintaining the positional relationship of the sites.

Next, another DNA amplification and transcription is performed in the same manner as described hereinabove by using the copy substrate 12 as a mother substrate. This procedure is repeated as many times as desired to thereby produce a large number of replications in geometric progression, such as shown in FIG. 2(C). Alternatively, it is possible to produce a large number of replications from a single mother substrate (i.e. DNA chip 11) alone by performing DNA amplification and transcription. The PCR may be applied with the mother substrate and copy substrate coupled together.

Figure 3:
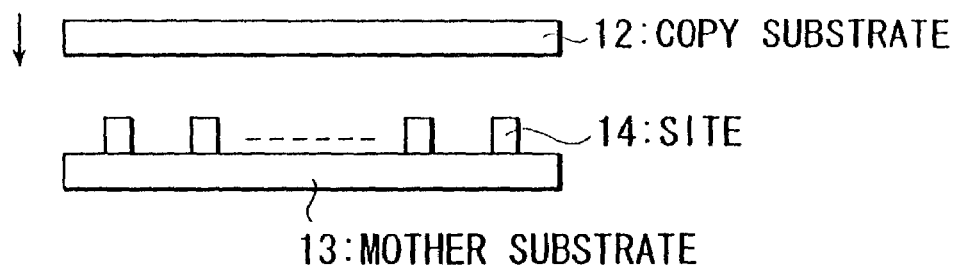
FIG. 3 is a view depicting a second illustrative embodiment of the method of the invention.

Mass production of the DNA chips can be accomplished as follows. (Note that DNA chips are referred to as an example. RNA, protein, sugar chains and the like are also covered by the invention) A plurality of porous sites 14, which may be sponge, for example, are attached to a mother substrate 13, as shown in FIG. 3, and soaked with a DNA solution. Then, pressure is applied and controlled to press the copy substrate onto the mother substrate 13, with the pressure being suitably controlled so that the amount of DNA solution being transferred in one transcription cycle is suitably regulated. It should be noted that the amount of DNA solution consumed by transcription on the mother substrate side is replenished by DNA amplification through the PCR.

Figure 4:
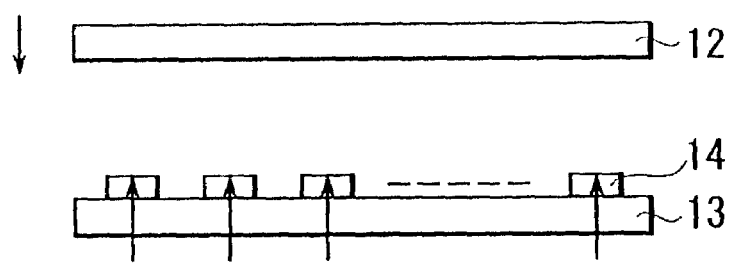
FIG. 4 is a view depicting a third illustrative embodiment of the method of the invention.

Alternatively, as shown in FIG. 4, the amount of DNA solution to be transcribed may be controlled by pressurizing or heating the backside of the mother substrate to squeeze the DNA solution out of the sites.

Figure 5:
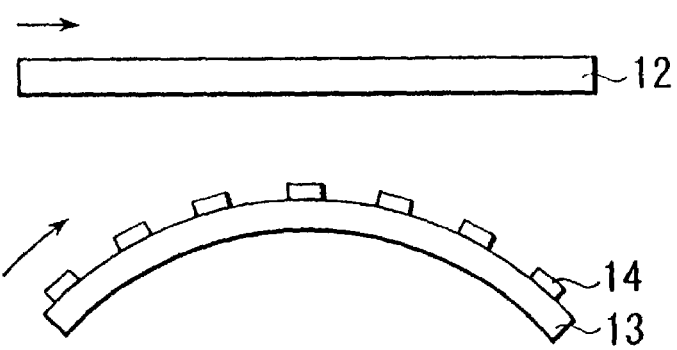
FIG. 5 is a view depicting a fourth illustrative embodiment of the method of the invention.

Also, it is possible to shape the mother substrate 13 to be in an arched shaped, as shown in FIG. 5, and rotated so that the DNA is transcribed to a copy substrate 12.

Figure 6:
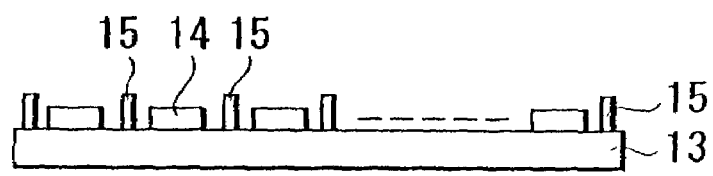
FIG. 6 is a view depicting a fifth illustrative embodiment of the method of the invention.

Moreover, as shown in FIG. 6, when applying PCR on the mother substrate 13, a separation wall may be formed between the sites, i.e. the DNA spots. Preferably, the separation wall 15 is made of a material that can be removed mechanically or chemically using light or gas after the completion of the PCR.

Figure 7:
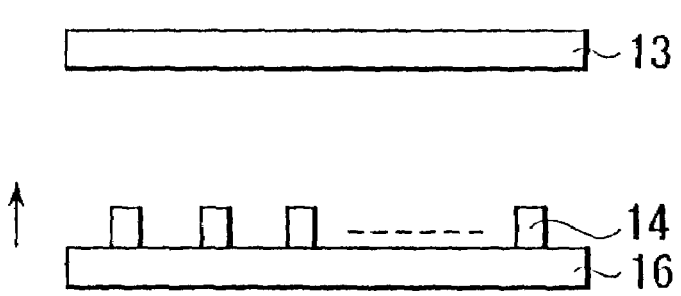
FIG. 7 is a view depicting a sixth illustrative embodiment of the method of the invention.

Furthermore, as shown in FIG. 7, transcription may be performed by first filling the sites (which are made of porous base material) on a master substrate 16 with a DNA solution for PCR and transferring the solution to the mother substrate 13 by contact therebetween. Next, the DNA deposited on the mother substrate 13 is PCR amplified and then transcribed to a copy substrate using the method depicted in FIG. 4, for example. The sites on the mother substrate 13 may be formed also by using porous base material and filled with the DNA solution for PCR. Then, the DNA deposited on the mother substrate 13 may be transcribed to a copy substrate by contact therebetween.

Figure 8:
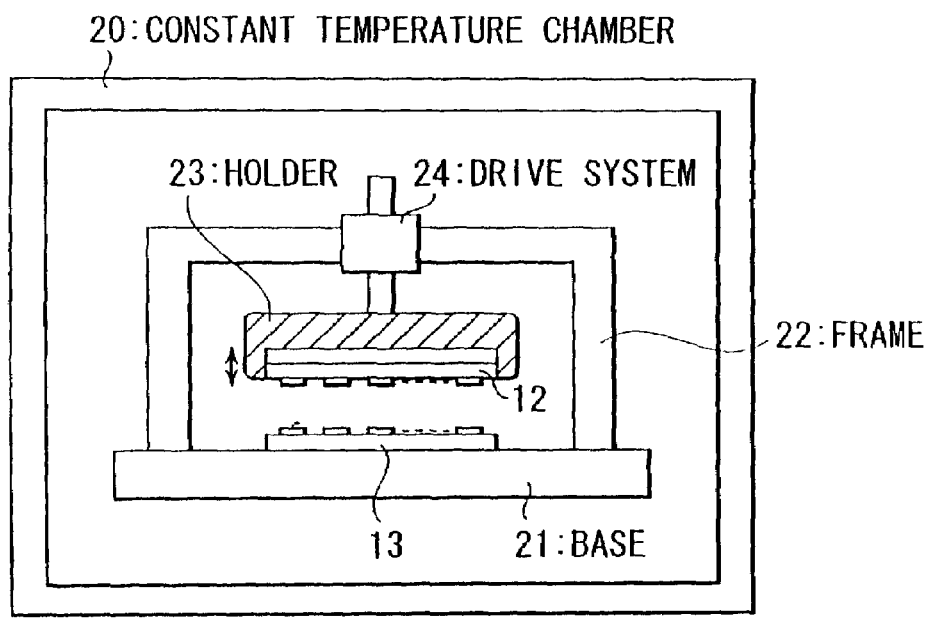
FIG. 8 is a view depicting a first illustrative embodiment of the apparatus of the invention.

FIG. 8 shows an apparatus for practicing the methods of the invention, wherein a temperature controllable constant temperature chamber 20 has contained therewithin a base 21 whereupon is disposed mother substrate 13; a frame 22 attached to base 21; a holder 23 for holding the copy substrate 12, and a drive system 24 for moving the holder 23 up and down. The drive system 24 is attached to frame 22. The mother substrate 13, which is a DNA chip, is positioned on the base 21 and the drive system 24 is actuated so that copy substrate 12 held by holder 23 is pressurized and brought into close direct contact with the mother substrate 13. The drive system 24 is also capable of controlling the pressure.

When transcription to the copy substrate 12 is completed, the drive system 24 is actuated to move up the holder 23 so that the copy substrate 12 is separated from the mother substrate 13 and then removed. The mother substrate is kept in place as it is. The amount of DNA solution consumed on the mother substrate side as a result of performing several transcription cycles is replenished by PCR amplification wherein the temperature of the constant temperature chamber 20 is lowered and raised. When the PCR amplification is completed, the temperature is reset to the predetermined level. By repeating the foregoing operation, it is possible to easily mass produce the DNA chips.

Figure 9:
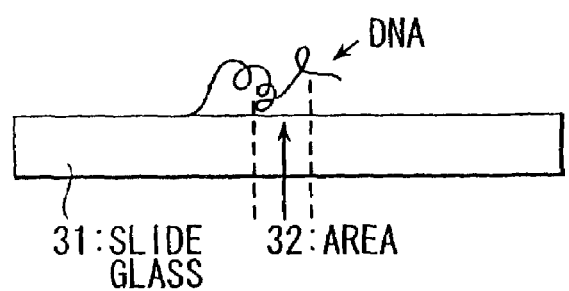
FIG. 9 is a view depicting entanglement of molecules on a substrate.

It should be noted that the prior art method of producing DNA chips by moving a pin and pressing the pin on the glass slide is designed to simply deposit a DNA solution on the slide and leave the deposited DNA solution to dry in the ambient surrounding. This method results in a problem in that a long sized DNA molecule becomes entangled, as shown in FIG. 9, or the molecule extends horizontally to hide an area 32 necessary for hybridization. This problem is solved by the embodiment discussed below.

First, the concept of the inventive method is explained with reference to FIGS. 10(A)–10(C). A pin 41, carrying a droplet of liquid containing DNA on its tip is pressed onto a glass slide 42 from the back side thereof, as shown in FIG. 10(A). When the pin 41 is removed, the droplet hangs down from the slide 42 due to gravity, as shown in FIG. 10(B). Then, the droplet settles in shape.

As shown in FIG. 10(B), an electrode 43 is placed on one side of slide 42 and an electrode 44 is placed on the other side of the glass slide 42. Voltage is applied across the two electrodes so that a negative charge is supplied to the electrode 43 and a positive charge is supplied to the electrode 44. Since the DNA is always electrified with a negative charge, each DNA molecule in the droplet extends toward the positive polarity as in the case of DNA electrophoresis. If the droplet is left to dry naturally, the DNA molecule will solidify, as shown in FIG. 10(C), without becoming entangled or causing the hiding of the area for hybridization. Thus, a chip with the DNA molecule extending downward is formed, that is hanging down perpendicularly.

Figure 11:
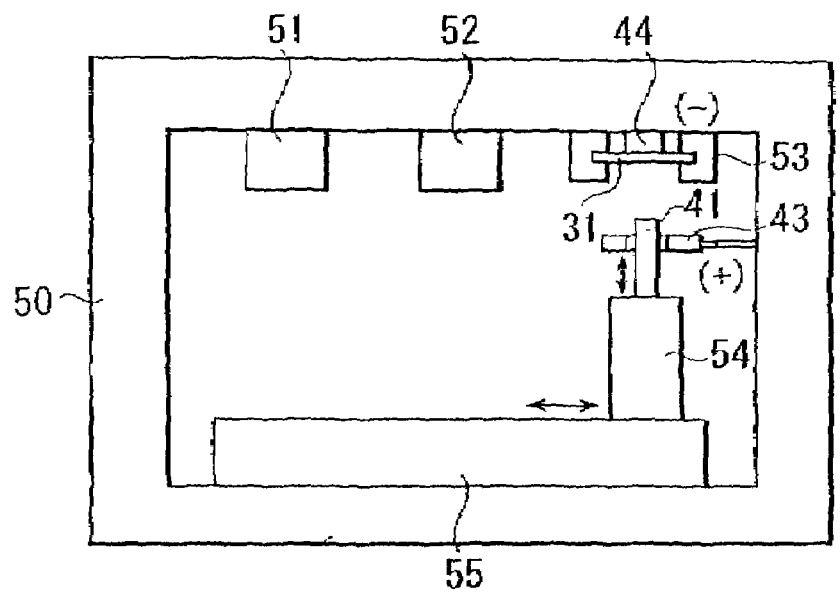
FIG. 11 is a view depicting a second illustrative embodiment of the apparatus of the invention.

FIG. 11 shows an apparatus to practice the method according to FIGS. 10(A)–10(C). In FIG. 11, a cleaning fluid unit 51, a solution unit 52 containing the DNA, a holder 53 which holds a glass slide 31, are arranged on the top of a frame 50. A pin holder 54 that holds a pin 41 is mounted on a stage 55 installed on the floor of the frame 50 so that the holder has free, lateral movement. The pin holder 54 can move the pin 41 up and down as desired. The cleaning fluid unit 51 and solution unit 52 securely retain the cleaning fluid and solution, respectively, and may comprise a sponge like material or means that take advantage of surface tension. Also, the electrodes 43 and 44 are disposed on the top surface of slide 31 and bottom surface thereof, respectively, so that the voltage is applied thereacross as desired. Also, a drying means (not shown in FIG. 11) for drying the DNA solution deposited on the slide 31 may be additionally disposed in the vicinity of the glass slide 31.

It should be noted that the drive and control means for sliding the pin holder 54 laterally across the stage 55 and for moving the pin 41 up and down, means for applying voltage across the electrodes 43 and 44, and means for actuating the drying means can be provided using known methods and devices.

The embodiment operates as follows. The pin 41 is lowered and the pin holder 54 is moved to a position directly under the cleaning fluid unit 51. The pin 41 is raised and the tip thereof is inserted into the cleaning fluid unit 51 and cleaned. The pin 41 is lowered again and the pin holder 54 is moved to a position directly under the solution unit 52. In this position, the pin 41 is raised to contact the contents of the solution unit 52 and a droplet of the solution is deposited on the tip of pin 41. After that, the pin 41 is lowered and the pin holder 54 is moved to a position directly under the glass slide 31. The pin 41 is then raised and pressed onto the bottom surface of the slide 31. Then, the pin 41 is lowered so that the tip thereof is lowered and the droplet is transferred onto the slide 31. Next, voltage is applied across the electrodes 43 and 44 so that the DNA molecule stretches toward the positive electrode 43. As a result of actuating the drying means under the foregoing condition, the DNA molecule continues to hang down from the glass slide 31, as shown in FIG. 10(C).

The instant invention is not limited to the embodiments above described. For example, a pin array comprising a plurality of pins may be used instead of a single pin. As an alternative, the cleaning fluid unit 51 and solution unit 52 may be located on the floor of frame 50 instead of on the ceiling thereof. Also, a washing chamber and a solution chamber (neither being shown in FIG. 11) may be used. In that case, the upside-down pin must be reset to the normal position, i.e. pointed downward, for cleaning and solution deposition. Both the positioning of the pin to be upside down and the electrifying of the DNA chip are not always necessary, but either one of the two alone may suffice. Although a pin is used in the embodiment to place spots of DNA solution on the glass slide, the spots may be deposited using a printing method instead.

Another alternative example involves applying voltage to the electrodes switched between the positive and negative polarities, as desired. With the switching, it is possible to untangle the DNA molecules. Moreover, in addition to the DNA the invention can be applied to RNA, protein and sugar chain molecules. Also, it is possible to prevent a DNA molecule deposited on a substrate from becoming entangled, thereby allowing the molecule to hang down from the substrate. Hence, it is possible with the invention to easily produce biochips in such a manner that the molecule does not hide the area necessary for hybridization.

Figure 12:
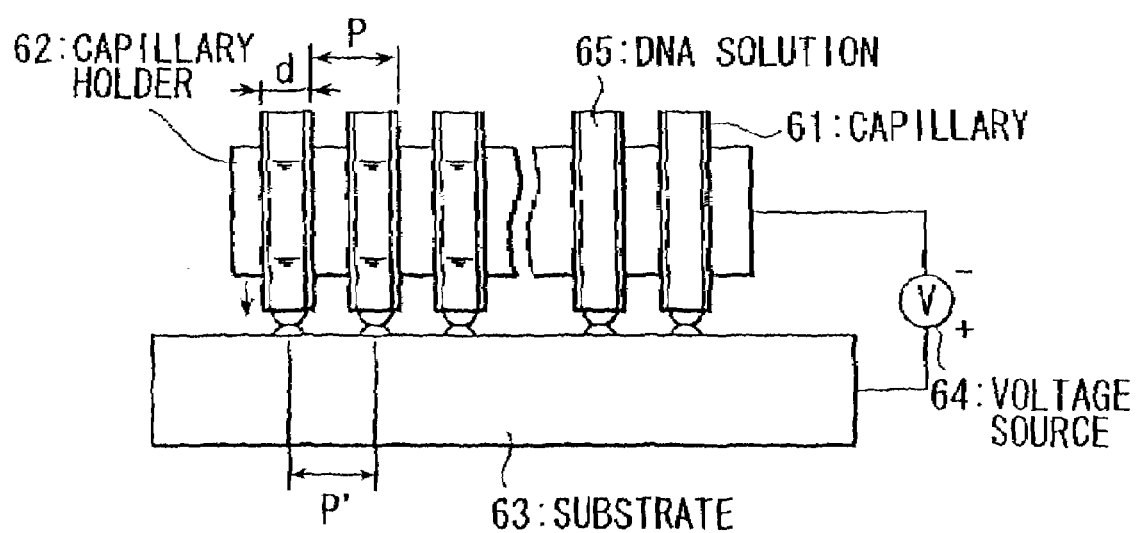
FIG. 12 is a view depicting a third illustrative embodiment of the apparatus of the invention.

Another embodiment is depicted in FIG. 12 involving a plurality of capillaries with open ends arranged in an array in such a manner that the ends are flush with one another on the same plane. Different types of DNA solution are injected into the capillaries as desired. The array of capillaries is positioned face to face against a planar substrate and voltage is applied across the array and the substrate. Thus, a DNA solution in each capillary swells out of the bottom end thereof caused by the effects of electric fields. This causes droplets of DNA solution, each being on a picoliter scale, to be deposited on the substrate. Using such method, it is possible to easily and quickly and inexpensively produce on a large scale DNA chips with uniform quality.

In FIG. 12, a plurality of capillaries 61 are mounted on a capillary holder 62 in an array at the same interval of spacing. A DNA solution 65 is then injected into each capillary 61. The type of capillary used for this purpose has the inside diameter of dimension d that prevents the DNA solution 65 from spilling out of the bottom of the capillary under normal conditions. A plurality of capillaries 61 are mounted vertically on the capillary holder 62 so that the bottom ends thereof are flush with one another on the same horizontal plane. A substrate 63 forms a structure of a DNA chip and a top surface thereof is formed to be planar. The substrate 63 is arranged so that the surface is parallel with the bottom end of the capillary 61. Either the capillary holder 62 or the substrate 63, or both, are disposed to be vertically mobile so that the gap between the bottom end of capillary 61 and substrate 63 can be varied as desired. A voltage source 64 is used to apply voltage across the capillary holder 62 and substrate 63. For example, a positive voltage level is applied to the substrate 63 and a negative voltage level is applied to the capillary holder 62. When voltage is applied, electric fields act upon the DNA solution inside the capillary 61, thereby causing the DNA solution to swell below the bottom end of the capillary 61 toward the substrate 63.

The apparatus of FIG. 12 is operated as follows. DNA segments (also called DNA solutions) are previously injected into a plurality of capillaries 61. Since capillary 61 is made of a sufficiently thin tubing with an inside diameter d, the solution will not overflow out of the bottom end of the capillary. This is because the surface tension of such thin tube surpasses (i.e. greater than) the gravitational force. The capillary holder 62 is brought close to the substrate 63 so that an appropriate gap is formed therebetween. Then, a suitable voltage is applied across the capillary holder 62 and the substrate 63. Hence, the DNA solution inside the capillary 61 swells below the bottom end of the capillary by the effects of the electric field, causing droplets of the DNA solution, each being on a picoliter scale, to be deposited on the substrate 63. After deposition, electrification is stopped and the capillary holder 62 is moved away from the substrate 63.

At this point, the spacing P of the array of capillaries can be adjusted to match the spacing P' between the target sites (or cells) on a DNA chip so that the DNA solution is deposited on all of the sites at one time. With this method, it is possible to quickly deposit volumetrically identical droplets of the DNA solution. This method also makes it easy to pipette very small amounts of DNA solution.

It should be noted that the inside diameter d of the capillary 61 can be of any dimension provided it is smaller than spacing P. Also, each capillary 61 may be pressurized with air or other means from the side opposite to substrate 63, instead of applying voltage. Moreover, the positional relationship between substrate 63 and capillary 61 may be reversed vertically. Positioning substrate 63 above capillary 61 is advantageous in that the substrate 63 is less likely then to become contaminated with dust.

Other alternatives are also possible to implement. For example PCR may be applied within a capillary. This is advantageous in that the only task required is simply to replenish each capillary with a common, amplification purpose solution, thus saving the cost of labor of supplying DNA solutions. Also, for temperature processing in the PCR it is possible to cycle the PCR process at higher speeds by means of an atmospheric temperature change or by heating using laser radiation. It should be noted that this invention is not limited to DNA chips; it being possible to use the invention for biochips of RNA, protein or sugar chain molecules, etc.

According to the invention, it is possible to deposit biomolecules on a plurality of sites on a substrate, all at the same time, by applying electric fields or pneumatic pressure to an array of capillaries containing the biomolecules. This method is advantageous in that the biochips can be produced easily, quickly and with reliably identical volume of deposited biomolecules. Also, a small amount of biomolecular solution can be pipetted with ease.

The foregoing is descriptive of the principles of the invention. Numerous extensions and modifications thereof would be readily apparent to the worker skilled in the art. All such extensions and modifications are to be considered to be within the spirit and scope of the invention.

What is claimed is:

1. A method for producing biochips by arranging one or more sites of DNA, RNA or protein in an array on a substrate having a front side and a back side, wherein DNA, RNA or protein chips are produced by a process comprising the steps of:

positioning at least one pin under, then into a cleaning fluid unit to clean said at least one pin;

repositioning said at least one pin under, then into a solution unit containing a solution of DNA, RNA or protein to provide a droplet of solution on said at least one pin;

repositioning said at least one pin under the substrate;

raising said at least one pin to contact the back side of said substrate;

lowering said at least on pin whereby said droplet is transferred to the back side of said substrate and hangs down from said substrate due to gravity;

applying an electric field to stretch DNA, RNA or protein in the solution toward a positive electrode under said substrate; and repeating the above steps to produce a biochip.

2. The method of claim 1, wherein a plurality of pins or a plurality of pins in an array are provided.

3. An apparatus for producing biochips by arranging one or more sites of DNA, RNA or protein in an array on a substrate having a back side and a front side, said apparatus comprising:

a pin holder comprising at least one pin;

a cleaning fluid unit for cleaning a tip of said at least one pin;

a solution unit for supplying a tip of said at least one pin with solution to be deposited;

a stage for moving said at least one pin to enable said cleaning unit to supply cleaning fluid to said tip to cause cleaning thereof and then, to obtain solution from said solution unit on at least a tip of said at least one pin; and then, to move said at least one pin to a desired position below said back side of said substrate to cause said at least one pin to deposit a droplet from said tip onto said backside of said substrate; and means for supplying electric current to a first electrode disposed on a surface of said front side of said substrate and a second electrode disposed on said backside of said substrate so as to enable said droplet of said solution on said tip of said at least one pin to be deposited onto and hang down from said back side of said substrate.

4. The apparatus of claim 3, wherein a plurality of pins or a plurality of pins in an array are provided.

* * * * *